(12) United States Patent
Yang et al.

(10) Patent No.: US 11,209,384 B2
(45) Date of Patent: Dec. 28, 2021

(54) ELECTROCHEMICAL SENSOR CONTAINING AN INTERNAL REFERENCE CELL

(71) Applicant: Carrier Corporation, Palm Beach Gardens, FL (US)

(72) Inventors: Zhiwei Yang, East Hartford, CT (US); Lei Chen, Farmington, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 132 days.

(21) Appl. No.: 16/342,464

(22) PCT Filed: Oct. 18, 2017

(86) PCT No.: PCT/US2017/057253
§ 371 (c)(1),
(2) Date: Apr. 16, 2019

(87) PCT Pub. No.: WO2018/075681
PCT Pub. Date: Apr. 26, 2018

(65) Prior Publication Data
US 2019/0257782 A1     Aug. 22, 2019

Related U.S. Application Data

(60) Provisional application No. 62/409,785, filed on Oct. 18, 2016.

(51) Int. Cl.
*G01N 27/407* (2006.01)
*G01N 27/417* (2006.01)
*G01N 33/00* (2006.01)

(52) U.S. Cl.
CPC ..... *G01N 27/4076* (2013.01); *G01N 27/4074* (2013.01); *G01N 27/4175* (2013.01); *G01N 33/007* (2013.01); *G01N 33/0063* (2013.01)

(58) Field of Classification Search
CPC ............. G01N 27/4076; G01N 33/007; G01N 27/4074; G01N 27/4175; G01N 33/0063; G01N 27/406–41; G01N 33/0004–0075
See application file for complete search history.

(56) References Cited

U.S. PATENT DOCUMENTS 4,394,222 A * 7/1983 Rohr .................. G01N 27/4065
204/406
4,724,061 A * 2/1988 Nyberg .............. G01N 27/4076
204/412

(Continued)

FOREIGN PATENT DOCUMENTS

DE      102005033727 A1    1/2007
EP          1288655 A2    3/2003

(Continued)

OTHER PUBLICATIONS

US 6,425,995 B1, 07/2002, Fletcher et al. (withdrawn)

(Continued)

*Primary Examiner* — Joshua L Allen
(74) *Attorney, Agent, or Firm* — Cantor Colburn LLP

(57) ABSTRACT

An electrochemical sensor is provided having a housing with an opening therein. The housing defines a chamber. The sensor includes a primary cell having a primary working electrode aligned with the opening in the housing so that the primary working electrode is exposed to an environment outside of the chamber. A primary counter electrode is sealed within the chamber. The sensor includes a secondary cell having a secondary working electrode sealed within the chamber, and a secondary counter electrode sealed within the chamber.

11 Claims, 10 Drawing Sheets

(56) References Cited

U.S. PATENT DOCUMENTS

| | | | |
|---|---|---|---|
| 5,098,545 A | | 3/1992 | Patko |
| 5,124,021 A | * | 6/1992 | Kaneyasu ............ G01N 27/417 204/425 |
| 5,215,644 A | * | 6/1993 | Ashikaga ............ G01L 19/0672 204/412 |
| 6,165,336 A | * | 12/2000 | Maki .................. G01N 27/4074 204/415 |
| 6,182,497 B1 | * | 2/2001 | Krajci ................ G01N 33/0075 73/23.2 |
| 6,214,206 B1 | | 4/2001 | Kriz |
| 6,409,909 B1 | | 6/2002 | Spichiger-Keller et al. |
| 6,416,653 B1 | | 7/2002 | Barben, II et al. |
| 6,471,840 B1 | * | 10/2002 | Gao .................. G01N 27/4175 204/425 |
| 6,599,409 B1 | | 7/2003 | Broadley et al. |
| 7,048,844 B2 | | 5/2006 | Chen et al. |
| 7,279,133 B2 | | 10/2007 | Chen et al. |
| 7,511,504 B2 | | 3/2009 | Pechstein et al. |
| 7,901,555 B2 | | 3/2011 | Jiang et al. |
| 9,217,724 B2 | | 12/2015 | Trappt et al. |
| 9,274,080 B2 | | 3/2016 | Auerswald et al. |
| 2005/0040038 A1 | | 2/2005 | Berger et al. |
| 2005/0252790 A1 | | 11/2005 | Dobson et al. |
| 2006/0049048 A1 | * | 3/2006 | Kondo ................ G01N 27/4074 204/425 |
| 2006/0278529 A1 | | 12/2006 | Feng et al. |
| 2008/0069177 A1 | | 3/2008 | Minor et al. |
| 2009/0145778 A1 | | 6/2009 | Allmendinger |
| 2011/0314898 A1 | | 12/2011 | Liemersdorik et al. |
| 2013/0161191 A1 | | 6/2013 | Wilhelm et al. |
| 2016/0178229 A1 | | 6/2016 | Chen et al. |
| 2017/0299543 A1 | * | 10/2017 | Akasaka .............. G01N 27/419 |
| 2019/0204282 A1 | * | 7/2019 | Gong ................ G01N 27/4175 |

FOREIGN PATENT DOCUMENTS

| | | |
|---|---|---|
| EP | 2639577 A1 | 9/2013 |
| WO | 2008004917 A1 | 1/2008 |
| WO | 2016008908 A1 | 1/2016 |

OTHER PUBLICATIONS

Fergus, Jeffrey W., "Solid electrolyte based sensors for the measurement of CO and hydrocarbon gases", Abstract, Sensors and Actuators B Chemical 122(2), Mar. 2007, 12 pages.

International Search Report and Written Opinion for application PCT/US2017/057253, dated Oct. 18, 2016, U301756US2, 14 pages Maas, S. et al., "Carbon support oxidation in PEM fuel cell cathodes", Abstract, Journal of Power Sources, vol. 176, Issue 2, Feb. 2008, 2 pages.

Fergus, Jeffrey W., "Solid electrolyte based sensors for the measurement of CO and hydrocarbon gases", Sensors and Actuators B Chemical 122(2), Mar. 2007, pp. 683-693.

Maas, S. et al., "Carbon support oxidation in PEM fuel cell cathodes", Journal of Power Sources, vol. 176, Issue 2, Feb. 2008, pp. 444-451.

* cited by examiner

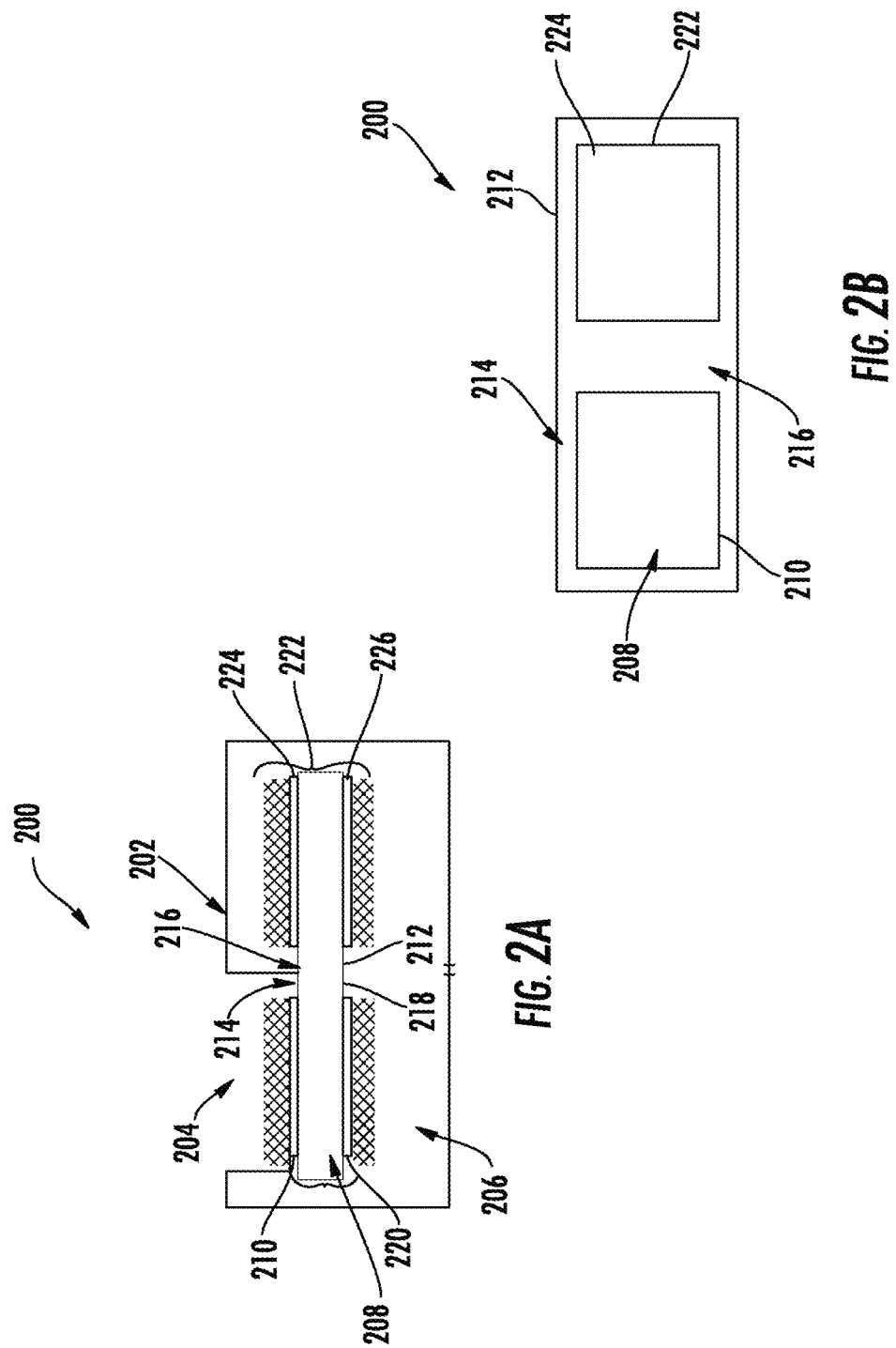

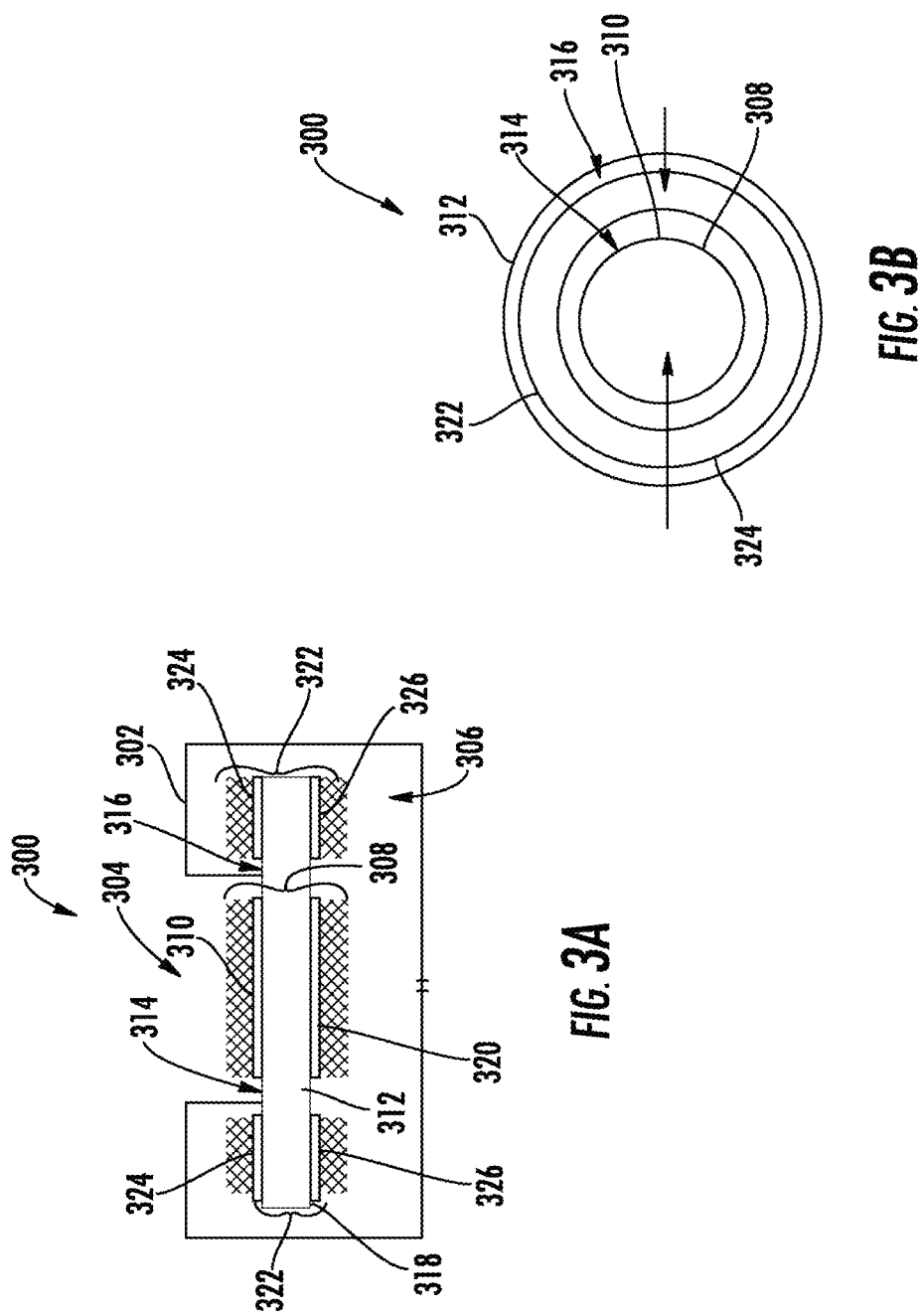

ELECTROCHEMICAL SENSOR CONTAINING AN INTERNAL REFERENCE CELL

CROSS REFERENCE TO RELATED APPLICATION

The present application is an international patent application, which claims priority to U.S. Patent Application Ser. No. 62/409,785, filed Oct. 18, 2016, which is herein incorporated in its entirety.

FIELD OF THE EMBODIMENTS

The present embodiments relate to electrochemical sensors and, more particularly, electrochemical sensors containing an internal reference cell.

BACKGROUND OF THE EMBODIMENTS

The next generation low global warming potential (LGWP) refrigerants, for example hydrofluoroolefins with a global warming potential of less than 30, are expected to enter the commercial and residential HVAC market in the near term. Nearly all of the new proposed LGWP refrigerants have an associated mild flammability, and are hence rated as A2L refrigerants. Sensors for leakage detection of flammable refrigerants are likely to be mandated by building codes in the future.

Electrochemical sensors are attractive due to their compact size, cost effectiveness, low power consumption and sensitivity. Solid polymer electrolyte electrochemical sensors have been used to detect various industrial and household toxic chemicals. An electrochemical senor generally includes a membrane electrode assembly having a working electrode, a counter electrode and a membrane sandwiched in-between. In order to electrochemically oxidize some types of hydrocarbon and hydrofluoroolefin refrigerants and produce a quantifiable current signal, a certain bias potential is needed. Generally, a positive bias potential is applied to the working electrode (vs. the counter electrode) of the electrochemical senor. If a target gas appears in the working environment, the gas will diffuse through a controlled opening on the sensor and reach the working electrode. This causes an electrochemical reaction on the electrodes, for example oxidation of the gas, which generates reaction current between the working electrode and the counter electrode. By monitoring the current, or the change of the current (by directly measuring current, or measuring the voltage converted from the current), the target gas concentration in the working environment can be calculated.

SUMMARY OF THE EMBODIMENTS

In one aspect, an electrochemical sensor is provided having a housing with an opening therein. The housing defines a chamber. The sensor includes a primary cell having a primary working electrode aligned with the opening in the housing so that the primary working electrode is exposed to an environment outside of the chamber. A primary counter electrode is sealed within the chamber. The sensor includes a secondary cell having a secondary working electrode sealed within the chamber, and a secondary counter electrode sealed within the chamber.

In a further aspect of the above, the sensor includes a substrate. The primary working electrode and the secondary working electrode are positioned on a first side of the substrate. The primary counter electrode and the secondary counter electrode are positioned on a second side of the substrate.

In a further aspect of any of the above, the sensor includes a primary substrate. The primary working electrode is positioned on a first side of the primary substrate, and the primary counter electrode is positioned on a second side of the primary substrate. The sensor also includes a secondary substrate. The secondary working electrode is positioned on a first side of the secondary substrate, and the secondary counter electrode is positioned on a second side of the secondary substrate.

In a further aspect of any of the above, the sensor includes a substrate. The substrate is sealed to the housing and aligned with the opening such that at least a portion of a first side of the substrate is exposed to the environment outside of the chamber and a second side of the substrate is sealed within the chamber. The primary working electrode is position on the portion of the first side of the substrate exposed to the environment outside of the chamber.

In a further aspect of any of the above, the sensor includes an aperture formed in the housing to maintain an environmental condition within the chamber.

In a further aspect of any of the above, at least one spacer maintains a position of the secondary cell with respect to the primary cell.

In a further aspect of any of the above, an electrically isolated material maintains a position of the secondary cell with respect to the primary cell.

In a further aspect of any of the above, a size of the opening is dependent on a surface area of the primary working electrode.

In a further aspect of the above, the primary counter electrode and the secondary counter electrode are formed as a unitary electrode.

In a further aspect of any of the above, the primary cell and the secondary cell have substantially the same baseline drift.

In one aspect, the primary working electrode is constructed and arranged to be exposed to target gases in the environment outside of the chamber. The primary counter electrode, the secondary working electrode, and the secondary counter electrode are constructed and arranged to be isolated from target gases in the environment outside of the chamber.

In a further aspect of the above, a gas detection device is provided having an electrochemical sensor. The sensor includes a housing having an opening therein. The housing defines a chamber. The sensor includes a primary cell comprising a primary working electrode aligned with the opening in the housing so that the primary working electrode is exposed to an environment outside of the chamber. A primary counter electrode is sealed within the chamber. The sensor also includes a secondary cell comprising a secondary working electrode sealed within the chamber, and a secondary counter electrode sealed within the chamber. The device also includes an alarm electrically coupled to the electrochemical sensor. The alarm is constructed and arranged to be triggered when the electrochemical sensor detects target gases in the environment outside of the chamber.

In a further aspect of any of the above, the primary working electrode and the secondary working electrode are positioned on a first side of a substrate, and the primary counter electrode and the secondary counter electrode are positioned on a second side of the substrate.

In a further aspect of any of the above, the primary working electrode is positioned on a first side of a primary substrate, and the primary counter electrode is positioned on a second side of the primary substrate. The secondary working electrode is positioned on a first side of a secondary substrate, and the secondary counter electrode positioned on a second side of the secondary substrate.

In a further aspect of any of the above, a substrate is sealed to the housing and aligned with the opening such that at least a portion of a first side of the substrate is exposed to the environment outside of the chamber and a second side of the substrate is sealed within the chamber. The primary working electrode is positioned on the portion of the first side of the substrate exposed to the environment outside of the chamber.

In a further aspect of any of the above, an aperture is formed in the housing to maintain an environmental condition within the chamber.

In a further aspect of any of the above, at least one spacer maintains a position of the secondary cell with respect to the primary cell.

In a further aspect of any of the above, an electrically isolated material maintains a position of the secondary cell with respect to the primary cell.

In a further aspect of any of the above, a size of the opening is dependent on a surface area of the primary working electrode.

In a further aspect of any of the above, the primary cell and the secondary cell have substantially the same baseline drift.

In a further aspect of any of the above, the primary working electrode is constructed and arranged to be exposed to target gases in the environment outside of the chamber, and the primary counter electrode, the secondary working electrode, and the secondary counter electrode are constructed and arranged to be isolated from target gases in the environment outside of the chamber.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIG. 2A is a side cross-sectional view of an electrochemical sensor in accordance with an embodiment.

FIG. 2B is a top cross-sectional view of a membrane electrode assembly of an electrochemical sensor in accordance with an embodiment.

FIG. 3A is a side cross-sectional view of an electrochemical sensor in accordance with an embodiment.

FIG. 3B is a top cross-sectional view of a membrane electrode assembly of an electrochemical sensor in accordance with an embodiment.

DETAILED DESCRIPTION OF THE EMBODIMENTS

Figure 1:
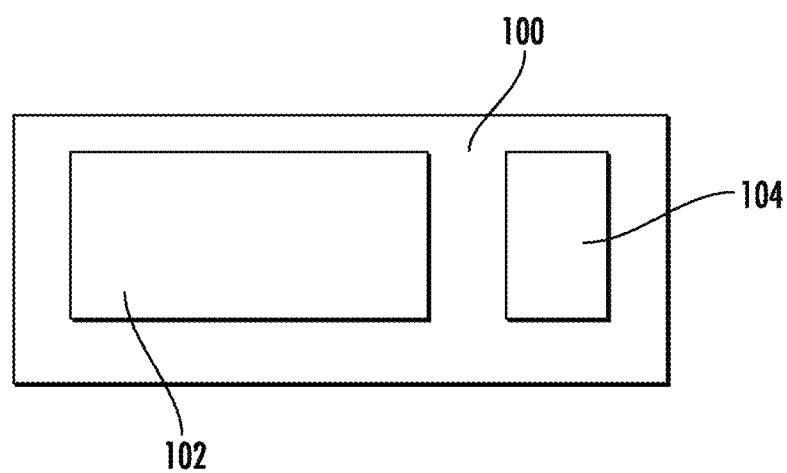
FIG. 1 is a schematic view of a gas detection device in accordance with an embodiment.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present embodiments provide an electrochemical sensor containing internal reference cell(s) for detecting flammable refrigerants (i.e. hydrocarbon, olefin and hydrofluoroolefin gases). The sensor can be constructed using two sets of electrodes including ion conducting polymer membranes. A first pair of electrodes, separated by an ion conducting polymer membrane, operates as a sensing cell. A second pair of electrodes, separated by an ion conducting polymer membrane and not directly exposed to the environment to be monitored, operates as a reference cell of the sensing cell to correct a reading registered by the sensing cell for accurate determination of the concentration of refrigerants. The sensing electrode can face the working environment and can be made of a proton-conducting ionomer impregnated with noble metal catalysts. The reference cell can be configured to have no exposure to the environment to be detected and to provide a response that is used to correct the sensing cell output. Such a correction can include baseline drift offset, humidity correction, or the like. The design and material selection of the electrochemical sensor can allow for the oxidation of target chemicals under a potential bias to produce a quantifiable response over a long period of time regardless of baseline drift and cross sensitivity to humidity and temperature.

The reference cell can be constructed using the same materials as the sensing cell, and is located on a counter electrode side of the sensor unit. The reference cell may not be directly exposed to the target refrigerants in the surrounding atmosphere.

However, once a bias potential is applied to the working electrode, a baseline current is generated. The magnitude of the baseline current can vary with the environmental conditions, for example temperature and humidity, and aging of the sensor element, leading to the change of the sensor performance. For example, baseline drift and/or sensor sensitivity variation could lead to sensing error and false alarms.

Tracking and compensating for the baseline drift allows accurate determination of target gas (i.e. refrigerants) concentrations, enabling reliable system control and effectively minimizing false alarms.

The same bias potential can be applied to the reference cell as the sensing cell to generate a baseline current, the magnitude of which is correlated with the sensing cell. Specifically, the baseline current of the reference cell tracks the baseline current of the sensing cell as environmental conditions such as humidity and temperature change. The baseline drift resulting from material degradation of the reference cell can mirror that of the sensing element, thereby providing a reference to compensate for baseline variation in the sensing element throughout the lifetime of the sensor.

FIG. 1 illustrates a gas detection device 100 having an electrochemical sensor 102 that is constructed and arranged to detect target gases, for example refrigerants, in an environment. An alarm 104 is electrically coupled to the electrochemical sensor 102. The alarm 104 is constructed and arranged to be triggered when the electrochemical sensor 102 detects target gases in the environment.

FIGS. 2A and 2B illustrate an electrochemical sensor 200 that may be used with the gas detection device 100. Electrochemical sensor 200 includes a housing 202 having an opening 204 therein. The opening 204 can include a plurality of openings. The housing 202 defines a chamber 206.

A primary cell 208 can be provided within the chamber 206. The primary cell 208 includes a substrate 212. The substrate 212 can be sealed to the housing 202 and aligned with the opening 204 such that at least a portion 214 of a first side 216 of the substrate 212 is exposed to the environment outside of the chamber 206 and a second side 218 of the substrate 212 is sealed within the chamber 206. A primary working electrode 210 is positioned on the first side 216 of the substrate 212. The primary working electrode 210 is positioned on the portion 214 of the first side 216 of the substrate 212 that is exposed to the environment outside of the chamber 206. The primary working electrode 210 is aligned with the opening 204 in the housing so that the primary working electrode 210 is exposed to an environment outside of the chamber 206. The size of the opening 204 in the housing 202 is dependent on a surface area of the primary working electrode 210.

A primary counter electrode 220 can be sealed within the chamber 206. The primary counter electrode 220 can be positioned on the second side 218 of the substrate 212. The primary counter electrode 220 can be electrically coupled to the primary working electrode 210. The current signal can be produced between the primary working electrode 210 and the primary counter electrode 220.

The sensor 200 can include a secondary cell 222. The secondary cell 222 includes a secondary working electrode 224 positioned on the first side 216 of the substrate 212. A secondary counter electrode 226 can be positioned on the second side 218 of the substrate 212. The both the secondary working electrode 224 and the secondary counter electrode 226 are sealed within the chamber 206. The secondary counter electrode 226 is electrically coupled to the secondary working electrode 224. The current signal is produced between the secondary working electrode 224 and the secondary counter electrode 226. The bias potential between the primary working electrode 210 and the primary counter electrode 220 can be substantially the same as the bias potential between the secondary working electrode 224 and the secondary counter electrode 226. Accordingly, the primary cell 208 and the secondary cell 222 have substantially the same baseline drift. The primary working electrode 210 can be constructed and arranged to be exposed to target gases in the environment outside of the chamber 206. The primary counter electrode 220, the secondary working electrode 224, and the secondary counter electrode 226 can be constructed and arranged to be isolated from target gases in the environment outside of the chamber 206.

Figure 2C:
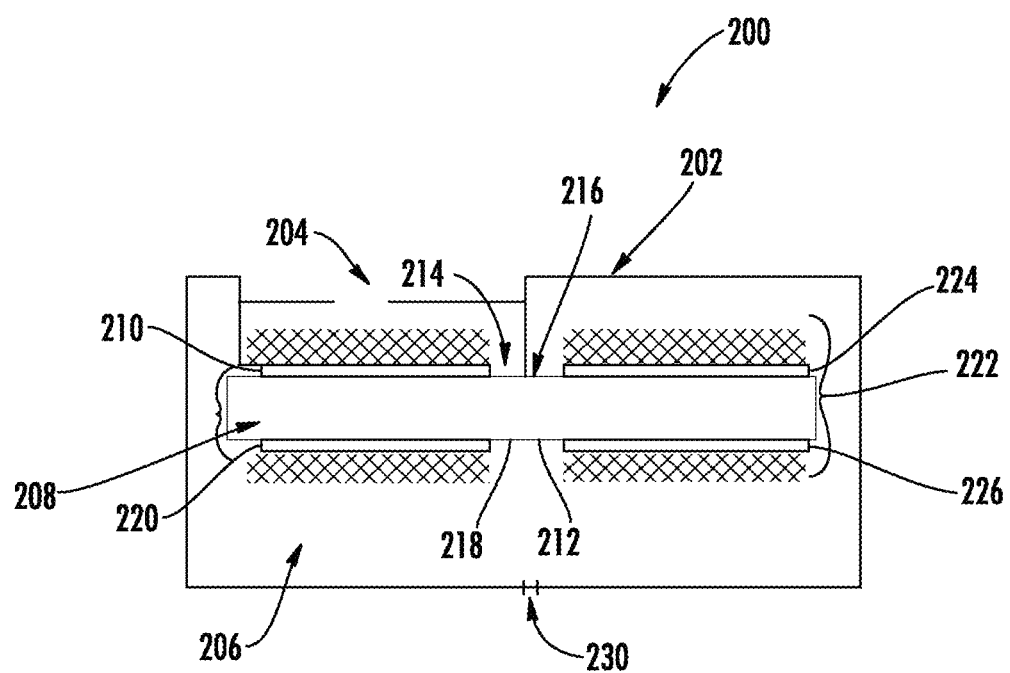
FIG. 2C is a side cross-sectional view of an electrochemical sensor in accordance with an embodiment.

The shown in FIG. 2C, the primary counter electrode 220 and the secondary counter electrode 226 may, or may not, need to stay in clean air in the isolated chamber 206, depending on the type of target gases. Some types of target gases influence the counter electrode performance, while, the others do not. The if the target gases do not influence the counter electrode performance (i.e. hydrofluoroolefins refrigerants), a controlled aperture 230 can be applied to better maintain an environmental condition within the portion of the chamber 206 where the primary counter electrode 220 and the secondary counter electrode 226 are positioned. The secondary working electrode 224 is isolated in a clean air portion of the chamber 206.

FIGS. 3A and 3B illustrate an electrochemical sensor 300 that may be used with the gas detection device 100. Electrochemical sensor 300 includes a housing 302 having an opening 304 therein. The opening 304 includes a plurality of openings. The housing 302 defines a chamber 306.

A primary cell 308 can be provided within the chamber 306. The primary cell 308 can include a substrate 312. The substrate 312 can be sealed to the housing 302 and aligned with the opening 304 such that at least a portion 314 of a first side 316 of the substrate 312 can be exposed to the environment outside of the chamber 306 and a second side 318 of the substrate 312 can be sealed within the chamber 306. A primary working electrode 310 can be positioned on the first side 316 of the substrate 312. The primary working electrode 310 can be positioned on the portion 314 of the first side 316 of the substrate 312 that is exposed to the environment outside of the chamber 306. The primary working electrode 310 can be aligned with the opening 304 in the housing so that the primary working electrode 310 can be exposed to an environment outside of the chamber 306. The size of the opening 304 in the housing 302 can be dependent on a surface area of the primary working electrode 310. In another embodiment, the primary counter electrode and the secondary counter electrode can be formed as a unitary electrode.

A primary counter electrode 320 can be sealed within the chamber 306. The primary counter electrode 320 can be positioned on the second side 318 of the substrate 312. The primary counter electrode 320 can be electrically coupled to the primary working electrode 310. The current signal can be produced between the primary working electrode 310 and the primary counter electrode 320.

The sensor 300 can include a secondary cell 322. The secondary cell 322 includes a secondary working electrode 324 positioned on the first side 316 of the substrate 312. The secondary working electrode 324 can be positioned around, and, the substantially encircles the primary working electrode 310. A secondary counter electrode 326 can be positioned on the second side 318 of the substrate 312. The secondary counter electrode 326 can be positioned around, and, the substantially encircles the primary counter electrode 320. The both the secondary working electrode 324 and the secondary counter electrode 326 can be sealed within the chamber 306. The secondary counter electrode 326 can be electrically coupled to the secondary working electrode 324.

The current signal can be produced between the secondary working electrode 324 and the secondary counter electrode 326. The bias potential between the primary working electrode 310 and the primary counter electrode 320 can be substantially the same as the bias potential between the secondary working electrode 324 and the secondary counter electrode 326. Accordingly, the primary cell 308 and the secondary cell 322 have substantially the same baseline drift. The primary working electrode 310 can be constructed and arranged to be exposed to target gases in the environment outside of the chamber 306. The primary counter electrode 320, the secondary working electrode 324, and the secondary counter electrode 326 can be constructed and arranged to be isolated from target gases in the environment outside of the chamber 306.

Figure 3C:
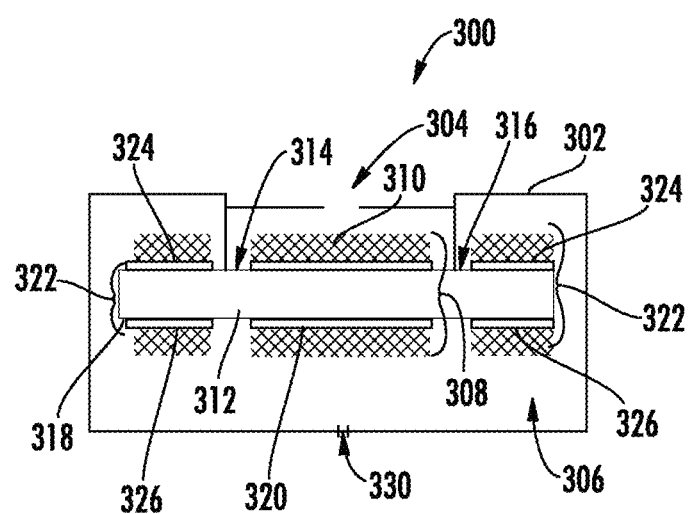
FIG. 3C is a side cross-sectional view of an electrochemical sensor in accordance with an embodiment.

The shown in FIG. 3C, the primary counter electrode 320 and the secondary counter electrode 326 may, or may not, need to stay in clean air in the isolated chamber 306, depending on the type of target gases. Some types of target gases influence the counter electrode performance, while, the others do not. Accordingly, the if the target gases do not influence the counter electrode performance (i.e. hydrofluoroolefins refrigerants), a controlled aperture 330 can be applied to better maintain an environmental condition within the portion of the chamber 306 where the primary counter electrode 320 and the secondary counter electrode 326 are positioned. The secondary working electrode 324 can be isolated in a clean air portion of the chamber 206.

Figure 4A:
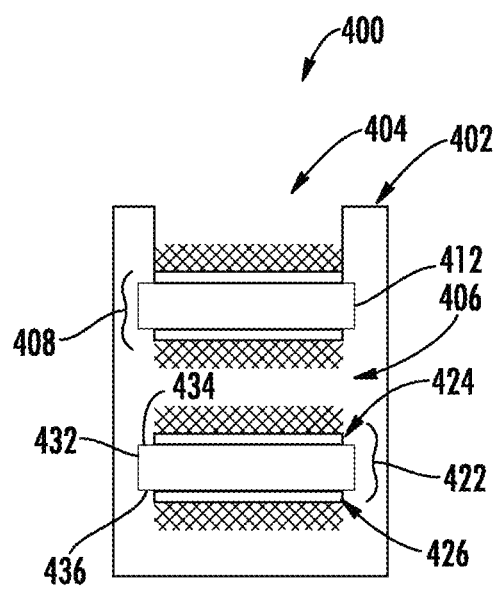
FIG. 4A is a side cross-sectional view of an electrochemical sensor in accordance with an embodiment.
Figure 4B:
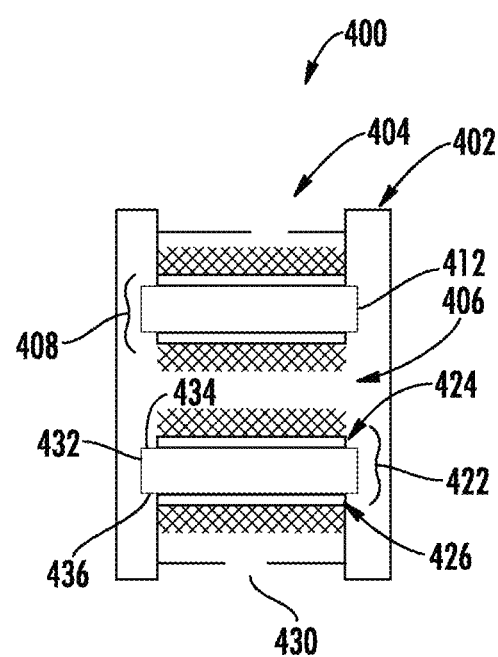
FIG. 4B is a side cross-sectional view of an electrochemical sensor in accordance with an embodiment.
Figure 5:
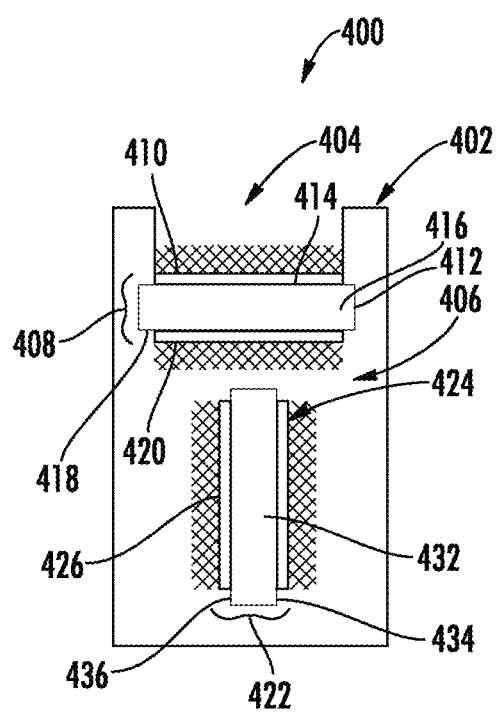
FIG. 5 is a side cross-sectional view of an electrochemical sensor in accordance with an embodiment.

FIGS. 4A, 4B, and 5 illustrate an electrochemical sensor 400 that may be used with the gas detection device 100. Electrochemical sensor 400 includes a housing 402 having an opening 404 therein. The opening 404 includes a plurality of openings. The housing 402 defines a chamber 406.

A primary cell 408 can be provided within the chamber 406. The primary cell can 408 include a primary substrate 412. The primary substrate 412 can be sealed to the housing 402 and aligned with the opening 404 such that at least a portion 414 of a first side 416 of the primary substrate 412 can be exposed to the environment outside of the chamber 406 and a second side 418 of the primary substrate 412 can be sealed within the chamber 406. A primary working electrode 410 can be positioned on the first side 416 of the primary substrate 412. The primary working electrode 410 can be positioned on the portion 414 of the first side 416 of the primary substrate 412 that is exposed to the environment outside of the chamber 406. The primary working electrode 410 can be aligned with the opening 404 in the housing so that the primary working electrode 410 is exposed to an environment outside of the chamber 406. The a size of the opening 404 in the housing 402 is dependent on a surface area of the primary working electrode 410.

A primary counter electrode 420 can be sealed within the chamber 406. The primary counter electrode 420 can be positioned on the second side 418 of the primary substrate 412. The primary counter electrode 420 can be electrically coupled to the primary working electrode 410. A current signal can be produced between the primary working electrode 410 and the primary counter electrode 420.

The sensor 400 can include a secondary cell 422. The at least one spacer (not shown) maintains a position of the secondary cell 422 with respect to the primary cell 408. An electrically isolated material (not shown) can maintain a position of the secondary cell 422 with respect to the primary cell 408. The secondary cell 422 can include a secondary substrate 432 having a first side 434 and a second side 436. FIG. 4 illustrates the secondary substrate 432 oriented substantially parallel to the primary substrate 412. FIG. 5 illustrates the secondary substrate 432 oriented substantially perpendicular to the primary substrate 412. The secondary substrate 432 may have any orientation with respect to the primary substrate 412. The secondary cell 322 includes a secondary working electrode 424 positioned on the first side 434 of the secondary substrate 432.

A secondary counter electrode 426 can be positioned on the second side 436 of the secondary substrate 432. The both the secondary working electrode 424 and the secondary counter electrode 426 can be sealed within the chamber 406. The secondary counter electrode 426 can be electrically coupled to the secondary working electrode 424. The current signal can be produced between the secondary working electrode 424 and the secondary counter electrode 426. The bias potential between the primary working electrode 410 and the primary second electrode 420 can be substantially the same as the bias potential between the secondary working electrode 424 and the secondary counter electrode 426. Accordingly, the primary cell 408 and the secondary cell 422 have substantially the same baseline drift. The primary working electrode 410 can be constructed and arranged to be exposed to target gases in the environment outside of the chamber 406. The primary counter electrode 420, the secondary working electrode 424, and the secondary counter electrode 426 are constructed and arranged to be isolated from target gases in the environment outside of the chamber 406.

The shown in FIG. 4B, the primary counter electrode 420 and the secondary counter electrode 426 may, or may not, need to stay in clean air in the isolated chamber 406, depending on the type of target gases. Some types of target gases influence the counter electrode performance, while, the others do not. If the target gases do not influence the counter electrode performance (i.e. hydrofluoroolefins refrigerants), a controlled aperture 430 can be applied to better maintain an environmental condition within the portion of the chamber 406 where the primary counter electrode 420 and the secondary working electrode 424 are positioned. The secondary working electrode 424 can be isolated in a clean air portion of the chamber 406.

Figure 6:
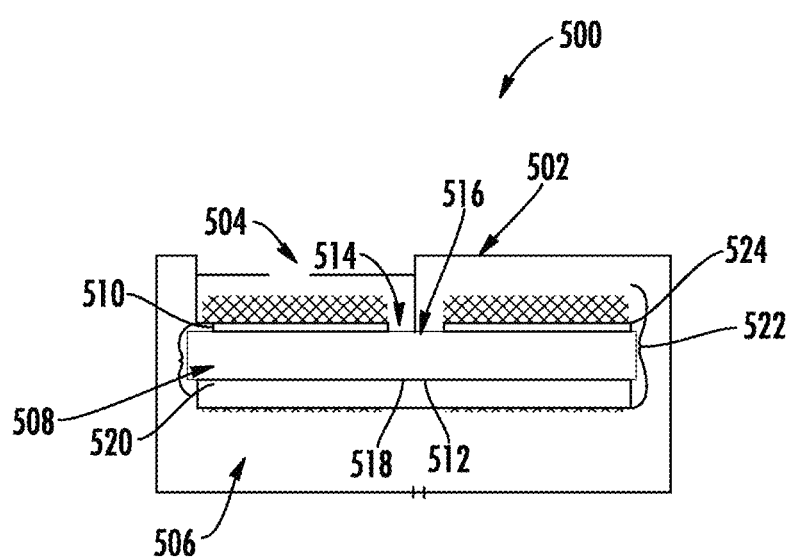
FIG. 6 is a side cross-sectional view of an electrochemical sensor in accordance with an embodiment.

FIG. 6A illustrates an electrochemical sensor 500 that may be used with the gas detection device 100. Electrochemical sensor 500 includes a housing 502 having an opening 504 therein. The opening 504 includes a plurality of openings. The housing 502 defines a chamber 506.

A primary cell 508 can be provided within the chamber 506. The primary cell 508 includes a substrate 512. The substrate 512 can be sealed to the housing 502 and aligned with the opening 504 such that at least a portion 514 of a first side 516 of the substrate 512 can be exposed to the environment outside of the chamber 506 and a second side 518 of the substrate 512 can be sealed within the chamber 506. A primary working electrode 510 can be positioned on the first side 516 of the substrate 512. The primary working electrode 510 can be positioned on the portion 514 of the first side 516 of the substrate 512 that can be exposed to the environment outside of the chamber 506. The primary working electrode 510 can be aligned with the opening 504 in the housing so that the primary working electrode 510 can be exposed to an environment outside of the chamber 506. The size of the opening 504 in the housing 502 can be dependent on a surface area of the primary working electrode 510.

A counter electrode 520 can be sealed within the chamber 506. The counter electrode 520 can be positioned on the second side 518 of the substrate 512. The counter electrode 220 is electrically coupled to the primary working electrode 510. The current signal can be produced between the primary working electrode 510 and the counter electrode 520.

The sensor 500 includes a secondary cell 522. The secondary cell 522 includes a secondary working electrode 524 positioned on the first side 516 of the substrate 512. The secondary working electrode 524 can be sealed within the chamber 506. The counter electrode 520 can be electrically coupled to the secondary working electrode 524. The current signal can be produced between the secondary working electrode 524 and the counter electrode 526. The bias potential between the primary working electrode 510 and the counter electrode 520 can be substantially the same as the bias potential between the secondary working electrode 524 and the counter electrode 520. Accordingly, the primary cell 508 and the secondary cell 522 have substantially the same baseline drift. The primary working electrode 510 can be constructed and arranged to be exposed to target gases in the environment outside of the chamber 506. The counter electrode 520 and the secondary working electrode 524 are constructed and arranged to be isolated from target gases in the environment outside of the chamber 506.

Figure 7:
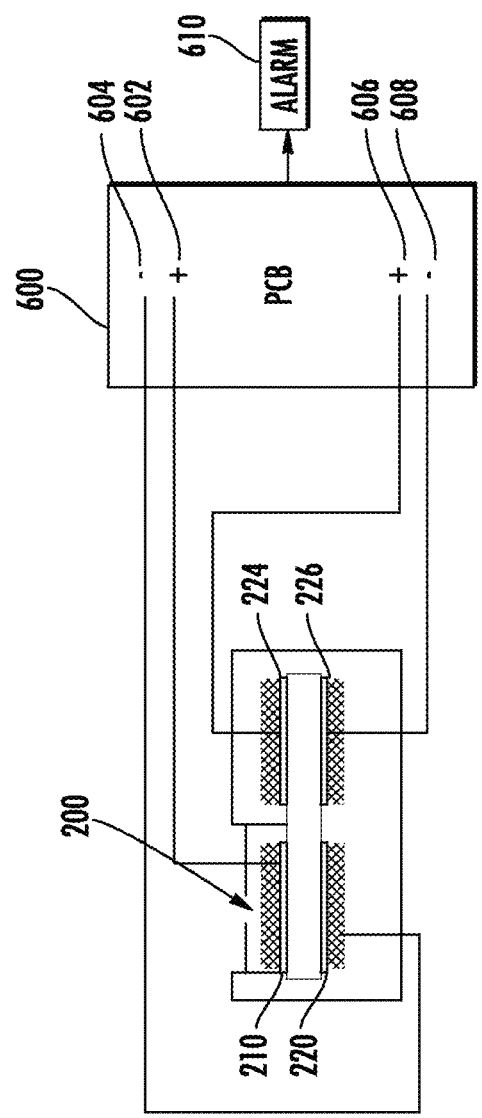
FIG. 7 is a side cross-sectional view of an electrochemical sensor electrically coupled to a circuit board in accordance with an embodiment.

FIG. 7 illustrates the electrochemical sensor 200 coupled to a circuit board 600. The primary working electrode 210 can be electrically coupled to a first positive terminal 602 of the circuit board 600, and the primary counter electrode 220 can be electrically coupled to a first negative terminal 604 of the circuit board 600. The secondary working electrode 224 can be electrically couple to a second positive terminal 606 of the circuit board 600, and the secondary counter electrode 226 can be electrically coupled to a second negative terminal 608 of the circuit board 600. The circuit board 600 can be electrically coupled to an alarm 610.

The circuit board 600 can provide a desired bias potential between the primary working electrode 210 and the primary counter electrode 220, and monitors the generated current there between. In a clean environment, i.e. no target gas, the measured current provides a primary cell baseline current. The circuit board 600 provides the same bias potential between the second working electrode 224 and the secondary counter electrode 226, and monitors the generated current there between at the same time to provide a secondary cell (or reference cell) baseline current.

The secondary cell 222 may be a different shape and/or size from the primary cell 208. The primary cell 208 and secondary cell 222 may be made from the same materials and with the same design/configuration, therefore, giving the same value of the current/cell size ratio (the baseline current is typically proportional to the cell/electrode size), and having the same baseline drift direction and drift percentage caused by environment conditions or the material's aging.

When the sensor 200 is exposed to target gases, a larger current may be generated and measured between the primary working electrode 210 and the primary counter electrode 220, while the secondary cell 222 does not see target gas and still gives a baseline current only. Therefore, by tracking the secondary cell baseline current, and according to the size ratio of the primary cell 208 to the secondary cell 222, proportionally extracting the primary cell's baseline current from its total current, the neat oxidation reaction current of target gases can be calculated, which is known to proportional to the gas concentrations. If the target gas concentration is detected to be higher than the desired threshold, the alarm 610 can be triggered.

The present embodiments may mitigate the negative impact of baseline drift and sensor degradation on the reliability of electrochemical sensors. The present embodiments may extend the useful lifetime of electrochemical sensors. The present embodiments may be utilized with low global warming potential refrigerants sensors or the like.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:
1. An electrochemical sensor comprising:
  a housing comprising an opening therein, the housing defining a chamber;
  a primary cell comprising:
    a primary working electrode aligned with the opening in the housing so that the primary working electrode is exposed to an environment outside of the chamber, and
    a primary counter electrode sealed within the chamber;
  a secondary cell comprising:
    a secondary working electrode sealed within the chamber, and
    a secondary counter electrode sealed within the chamber; and
  a substrate, the primary working electrode and the secondary working electrode positioned on a first surface of the substrate, and the primary counter electrode and the secondary counter electrode positioned on a second surface of the substrate opposite from the first surface of the substrate;
  wherein the primary counter electrode, the secondary working electrode, and the secondary counter electrode are positioned inside the chamber, the chamber being a single, common chamber housing all of the primary counter electrode, the secondary working electrode, and the secondary counter electrode;
  wherein the primary working electrode is located outside of the chamber.

2. The electrochemical sensor of claim 1, wherein the substrate is sealed to the housing and aligned with the opening such that at least a portion of the first surface of the substrate is exposed to the environment outside of the chamber and the second surface of the substrate is sealed within the chamber, the primary working electrode positioned on the portion of the first surface of the substrate exposed to the environment outside of the chamber.

3. The electrochemical sensor of claim 1, further comprising an aperture formed in the housing to maintain an environmental condition within the chamber.

4. The electrochemical sensor of claim 1, wherein the primary counter electrode and the secondary counter electrode are formed as a unitary electrode.

5. The electrochemical sensor of claim 1, wherein the primary cell and the secondary cell have substantially the same baseline drift.

6. The electrochemical sensor of claim 1, wherein a response is derived by comparing an output from the primary working electrode with an output of the secondary working electrode.

7. A gas detection device comprising:
  an electrochemical sensor comprising:
    a housing comprising an opening therein, the housing defining a chamber;
    a primary cell comprising a primary working electrode aligned with the opening in the housing so that the primary working electrode is exposed to an environment outside of the chamber, and a primary counter electrode sealed within the chamber,
    a secondary cell comprising a secondary working electrode sealed within the chamber, and a secondary counter electrode sealed within the chamber;
    a substrate, the primary working electrode and the secondary working electrode positioned on a first surface of the substrate, and the primary counter electrode and the secondary counter electrode positioned on a second surface of the substrate opposite from the first surface of the substrate; and
  an alarm electrically coupled to the electrochemical sensor, the alarm constructed and arranged to be triggered when the electrochemical sensor detects target gases in the environment outside of the chamber;

wherein the primary counter electrode, the secondary working electrode, and the secondary counter electrode are positioned inside the chamber, the chamber being a single, common chamber housing all of the primary counter electrode, the secondary working electrode, and the secondary counter electrode;

wherein the primary working electrode is located outside of the chamber.

8. The gas detection device of claim 7, wherein the substrate is sealed to the housing and aligned with the opening such that at least a portion of the first surface of the substrate is exposed to the environment outside of the chamber and the second surface of the substrate is sealed within the chamber, the primary working electrode positioned on the portion of the first surface of the substrate exposed to the environment outside of the chamber.

9. The gas detection device of claim 7, further comprising an aperture formed in the housing to maintain an environmental condition within the chamber.

10. The gas detection device of claim 7, wherein the primary counter electrode and the secondary counter electrode are formed as a unitary electrode.

11. The gas detection device of claim 7, wherein the primary cell and the secondary cell have substantially the same baseline drift.

* * * * *